United States Patent [19]

Lehrich et al.

[11] Patent Number: 5,621,138
[45] Date of Patent: Apr. 15, 1997

[54] 4-SUBSTITUTED BIS (2,6-DIISOPROPYLPHENYL)-CARBODIIMIDES, THEIR PREPARATION, THEIR USE, AND 4-SUBSTITUTED 2,6-DIISOPROPYLPHENYL ISOCYANATES WHICH CAN BE USED FOR THEIR PREPARATION

[75] Inventors: Friedhelm Lehrich, Lemfoerde; Siegmund Pohl; Bernd Bruchmann, both of Ludwigshafen; Helmut Tesch, Roedersheim-Gronau; Roland Minges, Gruenstadt; Johann Swoboda, Ludwigshafen; Manfred Genz, Damme; Guenter Scholz, Lemfoerde; Joachim Streu, Dachau, all of Germany

[73] Assignee: BASF Aktiengesellschaft, Germany

[21] Appl. No.: 593,100

[22] Filed: Jan. 30, 1996

Related U.S. Application Data

[62] Division of Ser. No. 494,452, Jun. 26, 1995, abandoned, which is a division of Ser. No. 126,292, Sep. 24, 1993, Pat. No. 5,532,414.

[30] Foreign Application Priority Data

Nov. 11, 1992 [DE] Germany .......................... 42 38 046.4

[51] Int. Cl.⁶ .................................................. C07C 265/12
[52] U.S. Cl. .......................... 560/358; 252/401; 252/403; 524/195; 525/907; 528/48; 554/5; 554/6; 560/3; 560/4; 564/252
[58] Field of Search ............................... 560/358

[56] References Cited

U.S. PATENT DOCUMENTS

| | | | |
|---|---|---|---|
| 2,853,473 | 9/1958 | Campbell et al. | 260/77.5 |
| 2,853,518 | 9/1958 | Balon | 260/551 |
| 3,193,523 | 7/1965 | Neumann et al. | 260/45.9 |
| 3,522,303 | 7/1970 | Ulrich | 260/551 |
| 3,632,620 | 1/1972 | Kober et al. | 564/252 |
| 3,644,456 | 2/1972 | Uhlrich | 260/453 AR |

OTHER PUBLICATIONS

EPO Search Report, Feb. 16, 1994.

Primary Examiner—Peter O'Sullivan

[57] ABSTRACT 4,4'-disubstituted bis-(2,6-diisopropylphenyl)carbodiimides of the formula (I)

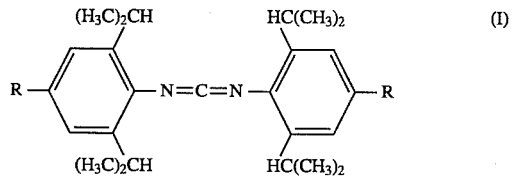

where R is 1-methyl-1-phenylethyl, phenoxy or tert-butyl, a process for their preparation, their use as stabilizers against hydrolytic degradation of polyaddition and polycondensation products containing ester groups, and the novel 4-(1-methyl-1-phenylethyl)-2,6-diisopropyl-, 4-phenoxy-2,6-diisopropyl- and 4-tert-butyl-2,6-diisopropylphenyl isocyanates which can be used for their preparation.

1 Claim, No Drawings

4-SUBSTITUTED BIS (2,6-DIISOPROPYLPHENYL)-CARBODIIMIDES, THEIR PREPARATION, THEIR USE, AND 4-SUBSTITUTED 2,6-DIISOPROPYLPHENYL ISOCYANATES WHICH CAN BE USED FOR THEIR PREPARATION

This is a divisional of application Ser. No. 08/494,452 filed on Jun. 26, 1995, now abandoned which is a divisional of application Ser. No. 08/126,292 filed Sep. 24, 1993, now U.S. Pat. No. 5,532,414.

The present invention relates to novel 4,4'-disubstituted bis(2,6-diisopropylphenyl)carbodiimides of the formula (I)

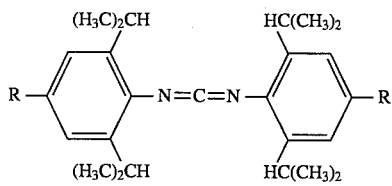

where R is 1-methyl-1-phenylethyl, phenoxy or tert-butyl, to a process for their preparation, to their use as stabilizers against hydrolytic degradation of polyaddition products and polycondensation products containing ester groups, and to the novel monoisocyanates of the formula (II)

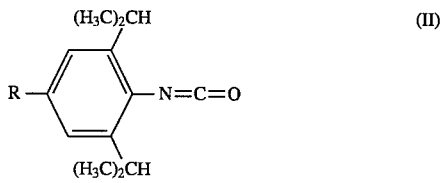

where R is as defined above, which can be used for their preparation.

Organic carbodiimides are known. Their chemistry is described, for example, in Chemical Reviews, Vol. 53 (1953), pages 145 to 166, and Angewandte Chemie 74 (1962), pages 801 to 806.

Monocarbodiimides and oligomeric polycarbodiimides can be prepared, for example, by treating sterically hindered monoisocyanates or polyisocyanates with basic catalysts with elimination of carbon dioxide. Examples of suitable basic catalysts are, according to GB-A-1,083,410, heterocyclic compounds containing bonded phosphorus, and, according to DE-B-1 130 594 (GB-A-851,936), phospholenes and phospholidines, and oxides and sulfides thereof.

Furthermore, polycarbodiimides containing terminal urethane groups are described, for example, in U.S. Pat. No. 2,941,983 and DE-B-22 48 751 (U.S. Pat. No. 4,076,945). The products can be prepared, for example, by carbodiimidation of diisocyanates containing sterically hindered isocyanate groups and subsequent partial or full urethanization of the terminal NCO groups using alcohols. If aromatic diisocyanates containing isocyanate groups of differing reactivity are used, all or some of the isocyanate groups of relatively high reactivity can first be convened into the corresponding urethane groups using alcohol, and the remaining isocyanate groups can then be convened into carbodiimide groups with elimination of carbon dioxide. Oligomeric carbodiimides having a mean degree of condensation of from 2 to 30, which are obtainable by oligo condensation of 2,4'-diisocyanatodiphenylmethane or of a 3,3',5,5'-tetra-$C_1$- to -$C_4$-alkyl-4,4'-diisocyanatodiphenylmethane or of mixtures of these unsubstituted or alkyl-substituted diisocyanatodiphenylmethanes with further difunctional or polyfunctional aromatic isocyanates and, if desired, reacting all or some of the remaining free isocyanate groups of the resultant oligomeric carbodiimides with an aliphatic, araliphatic or cycloaliphatic alcohol or amine, are described in DE-A-41 26 359.

The carbodiimides are preferably used as stabilizers against hydrolytic cleavage of polyester-based plastics. According to DE-A-1 494 009 (U.S. Pat. No. 3,193,523), suitable compounds for this purpose are, in particular, 2- and 2'-substituted aromatic and/or cycloaliphatic monocarbodiimides, for example 2,2',6,6'-tetraisopropyldiphenylcarbodiimide. Polycarbodiimides having a molecular weight of greater than 500 and containing more than 3 carbodiimide groups are described in DE-B-1 285 747 (U.S. Pat. No. 3,193,522) as heat and moisture stabilizers in plastics containing ester groups. Although substantial stability of plastics containing ester groups against moist heat, water and water vapor can be achieved by adding these (poly)carbodiimides as stabilizers, the products also have disadvantages. The disadvantages of the tetra-alkyl-substituted monocarbodiimides which are preferred industrially, for example 2,2', 6,6'-tetraisopropyldiphenylcarbodiimide, are their relatively high vapor pressure and, due to the low molecular weight, their tendency to migrate out of the polyaddition products, for example thermoplastic polyurethanes (TPUs), or polycondensation products, eg. polyterephthalates. This deficiency can be overcome, according to EP-A-0 460 481 (CA-A-2,043,820), by using substituted monocarbodiimides or oligomeric, substituted polycarbodiimides containing terminal isocyanate groups, which are prepared from substituted diisocyanates and which eliminate virtually no toxic, volatile substances either at elevated temperature, for example under conventional processing conditions, nor at room temperature. Polycarbodiimides of this type have relatively high melting points or are infusible and can only be introduced into the polyurethanes and/or their starting materials using complex equipment and at the expense of a considerable amount of time. Distribution of the polycarbodiimides in the plastics containing ester groups is therefore frequently insufficiently homogeneous, so that the stabilizer activity does not meet expectations. Although conversion of some of the terminal isocyanate groups into urethane groups, for example in accordance with DE-A-22 48 751 or U.S. Pat. No. 2,941,983, allows lower-melting polycarbodiimide derivatives to be obtained, not only does this additional reaction step make the products more expensive, but the attendant increase in molecular weight also results in a reduction in the content of active carbodiimide groups for a given account.

It is an object of the present invention to fully or at least partially overcome the abovementioned disadvantages and to provide antihydrolysis agents which are homogeneously soluble in plastics containing ester groups, preferably polyurethanes and in particular TPU, without additional homogenization steps being necessary to this end.

We have found that, surprisingly, this object is achieved by using selected trisubstituted phenyl isocyanates for the preparation of the carbodiimides.

The present invention accordingly provides 4,4'-disubstituted bis(2,6-diisopropylphenyl)carbodiimides of the formula (I)

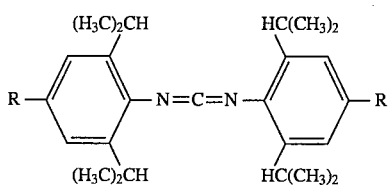

where R is 1-methyl-1-phenylethyl, phenoxy or tert-butyl.

Monocarbodiimides having a structure of the formula (I) are 4,4'-di(1-methyl-1-phenylethyl)-2,2',6,6'-tetraisopropyl-diphenylcarbodiimide, of the formula

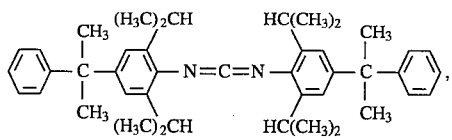

4,4'-diphenoxy-2,2',6,6'-tetraisopropyldiphenylcarbodiimide, of the formula

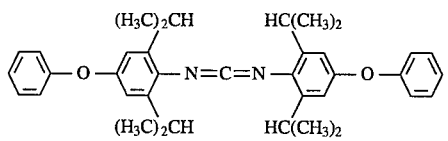

and 4,4'-di-tert-butyl-2,2',6,6'-tetraisopropyldiphenylcarbodiimide, of the formula

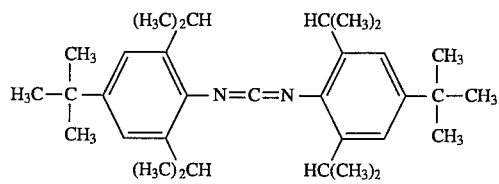

The present invention furthermore provides a process for the preparation of the 4,4'-disubstituted bis(2,6-diisopropylphenyl)carbodiimides of the formula (I) by condensing 4-substituted 2,6-diisopropylphenyl isocyanates in the presence of catalysts, wherein the 4-substituted 2,6-diisopropylphenyl isocyanates have a structure of the formula (II)

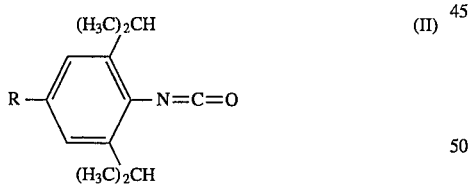

where R is 1-methyl-1-phenylethyl, phenoxy or tert-butyl, and the use of the 4,4'-disubstituted bis(2,6-diisopropylphenyl)carbodiimides of the formula (I) as stabilizers against hydrolyric degradation of polyaddition or polycondensation products containing bonded ester groups, and the 4-substituted 2,6-diisopropylphenyl isocyanates of the formula (II)

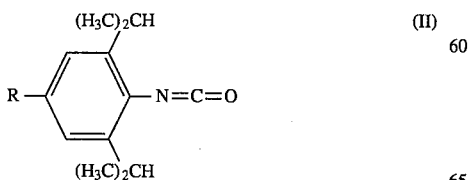

where R is 1-methyl-1-phenylethyl, phenoxy or tert-butyl, which can be used for the preparation of the novel 4,4'-disubstituted bis(2,6-diisopropylphenyl)carbodiimides of the formula (I).

The antihydrolysis action of the novel 4,4'-disubstituted bis(2,6-diisopropylphenyl)carbodiimides is at least comparable with that of the carbodiimides used industrially. If industrial safety procedures are followed, they can be metered economically without problems and without additional homogenization steps end introduced into the plastics containing ester groups, preferably polyurethanes. The novel carbodiimides have a relatively low vapor pressure and undergo negligible migration. It is also noteworthy that undesired side reactions, as can occur, for example, in the preparation of polycarbodiimides from diisocyanates due to undesired cyclization or polymerization thereof, are avoided by the use of 4-substituted 2,6-diisopropylphenyl isocyanates.

The 4-substituted 2,6-diisopropylphenyl isocyanates of the formula (II)

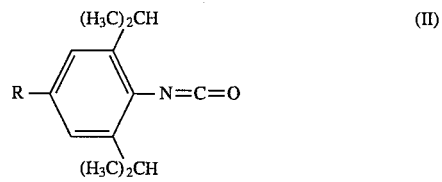

where R is 1-methyl-1-phenylethyl, phenoxy or tert-butyl, on which the novel carbodiimides are based are themselves novel. Said novel isocyanates have the following structural formulae:

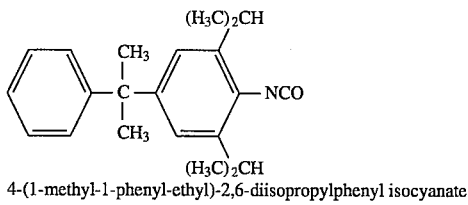
4-(1-methyl-1-phenyl-ethyl)-2,6-diisopropylphenyl isocyanate

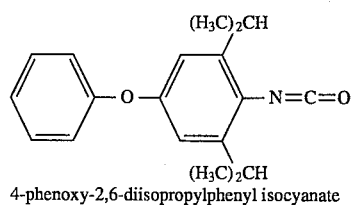
4-phenoxy-2,6-diisopropylphenyl isocyanate and

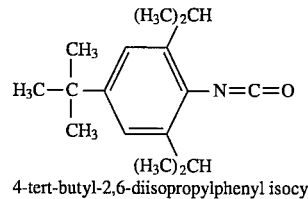
4-tert-butyl-2,6-diisopropylphenyl isocyanate

The 4-substituted 2,6-diisopropylphenyl isocyanates can be prepared by known processes, for example by reacting the appropriately 4-substituted 2,6-diisopropylanilines with phosgene, expediently in the presence of solvents which are inert under the reaction conditions, usually at below 100° C., preferably below 50° C., to give carbamoyl chlorides of the formula (III)

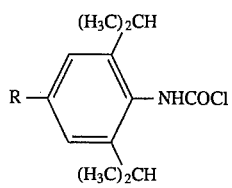

where R is as defined above, and subsequently thermalizing the resultant 4-substituted 2,6-diisopropylphenylcarbamoyl chlorides, usually at above 100° C., preferably at from 110° to 160° C., to give the novel 4-substituted 2,6-diisopropylphenyl isocyanates or by reacting the 4-substituted 2,6-diisopropylanilines with urea in the presence of alcohols and/or carbamates, in the presence or absence of alcohols, usually at from 100° to 200° C., preferably at from 125° to 175° C., to give 4-substituted 2,6-diisopropylphenylcarbamates of the formula (IV)

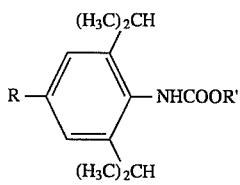

where R is as defined above, and R' is linear or branched alkyl having 1 to 12 carbon atoms, cyclohexyl or phenyl, and subsequently thermalizing the 4-substituted 2,6-diisopropylphenylcarbamates in the gas or liquid phase at above 150° C. to give the novel 4-substituted 2,6-diisopropylphenyl isocyanates.

The novel 4,4'-disubstituted bis(2,6-diisopropylphenyl) carbodiimides can be prepared by condensing the above-mentioned 4-substituted 2,6-diisopropylphenyl isocyanates at elevated temperature, for example at from 50° to 209° C., preferably at from 130° to 175° C., expediently in the presence of catalysts, with elimination of carbon dioxide. Processes which are suitable for this purpose are described, for example, in GB-A-1,083,410, DE-B-1 130 594 (GB-A-851,936) and DE-A-11 56 401 (U.S. Pat. No. 3,502,722). Examples of catalysts which have proven highly suitable are phosphorus compounds, preferably selected from the group consisting of phospholenes, phospholene oxides, phospholidines and phospholidine oxides. The carbodiimide formation is usually terminated when the reaction mixture contains less than 1% by weight of NCO groups. To this end, the catalysts can be removed by distillation under reduced pressure or deactivated by adding a deactivator, eg. phosphorus trichloride. The carbodiimide preparation can furthermore be carried out in the presence or absence of solvents.

The novel monocarbodiimides are highly suitable as acceptors for carboxyl compounds and are therefore preferably used as stabilizers against hydrolyric degradation of polycondensation products containing bonded ester groups, eg. polyesters, polyether esters, polyester amides and polycaprolactones, and polyaddition products containing bonded ester groups, such as polyurethanes, polyureas and polyurethane-polyurea elastomers. Due to their good solubility in the formative components for the preparation of polyurethanes and in the polyurethanes formed, the monocarbodiimides are particularly suitable as stabilizers against hydrolytic degradation of polyurethanes, preferably compact or cellular polyurethane elastomers and in particular TPU.

The concentration of the novel monocarbodiimides in the polycondensation or polyaddition products containing ester groups which are to be stabilized is generally from 0.05 to 10% by weight, preferably from 0.1 to 5% by weight. In individual cases, depending on the susceptibility of the plastic to hydrolysis, the concentration may be higher.

Various methods can be used to introduce the monocarbodiimides which can be used according to the invention into the polyaddition or polycondensation products containing ester groups which are to be stabilized. For example, the novel monocarbodiimides can be mixed with one of the formative components for the preparation of polyaddition products, eg. the polyisocyanates and/or polyhydroxyl compounds for the preparation of polyurethanes, or metered into the reaction mixture for the preparation of polyurethanes. In another procedure, the novel monocarbodiimides can be incorporated into the melt of the fully reacted polyaddition or polycondensation products. However, it is also possible to coat granules of the polyaddition or polycondensation products with the novel monocarbodiimides and to introduce these granules into the plastic compositions during subsequent production of moldings by melt extrusion. In a preferred embodiment, cast polyurethane elastomers and TPU on a polyesterpolyol basis are prepared by first treating the carboxyl-containing polyester-polyols with the novel monocarbodiimides in order to reduce the acid content and then reacting them, with or without the addition of further amounts of monocarbodiimides, with polyisocyanates, in the presence or absence of additional assistants and additives.

EXAMPLES

Preparation of 4-substituted 2,6-diisopropylphenyl isocyanates

Example 1

A solution of 99 g (1 mol) of phosgene in 1300 ml of monochlorobenzene was introduced into a 6000 ml laboratory phosgenation apparatus comprising a stirred vessel fitted with a stirrer, a reflux condenser with gas extractor, a dropping funnel and a mixing nozzle, and a solution of 252 g (0.85 mol) of 4-(1-methyl-1-phenyl-ethyl)-2,6-diisopropylaniline in 1300 ml of monochlorobenzene was fed in at below 50° C. through a nitrogen-flushed nozzle with vigorous stirring. In addition, 198 g (2 mol) of phosgene were added dropwise over a period of one hour.

Under these reaction conditions, known as cold phosgenation, no precipitation of the resultant 4-(1-methyl-1-phenyl-ethyl)-2,6-diisopropylanilinocarbamoyl chloride or hydrochloride was observed.

When all the amine solution had been added, the addition of phosgene was terminated and the pale-orange reaction solution was heated to 125° C. under reflux over the course of 1.75 hours. The excess phosgene and the monochlorobenzene were then removed from the reaction mixture by distillation, and the crude isocyanate formed was dechlorinated for one hour at 190° C./10 mbar.

272.3 g of a pale-brown crude product having an NCO content of 12.9% by weight (calculated 13.1% by weight) and a purity, determined by gas chromatography, of 95.8% by weight, a content of hydrolyzable chlorine of 111 ppm and a viscosity, measured at 25° C. by the Ubbelohde method, of 75 mPas, were obtained.

The resultant crude product was purified by distillation under reduced pressure, giving 4-(1-methyl-1-phenylethyl)-2,6-diisopropylphenyl isocyanate as a slightly milky liquid which boils at 135° C./0.5 mbar, in a yield of 98.6% of theory. The structure was determined by $^1$H-NMR and IR spectroscopy. Elemental analysis gave the following values:
C: calculated: 82.2% by weight; found: 81.9% by weight
H: calculated: 8.5% by weight; found: 8.6% by weight
N: calculated: 4.4% by weight; found: 4.8% by weight

Example 2

The procedure was similar to that of Example 1, but the amine used was 229 g (0.85 mol) of 4-phenoxy-2,6-diisopropylaniline, and dechlorination at 190° C./10 mbar was not carried out.

274.9 g of a dark-brown crude product having an NCO content of 14.0% by weight (calculated 14.2% by weight), a purity, determined by gas chromatography, of 98.3% by weight, a content of hydrolyzable chlorine of 600 ppm and a viscosity, measured at 25° C. by the Ubbelohde method, of 65 mPas, were obtained.

The resultant crude product was purified by distillation under reduced pressure, giving 4-phenoxy-2,6-diisopropylphenyl isocyanate as a clear, colorless liquid which boils at 134° C./0.5 mbar, in a yield of 97.8% of theory.

The structure was determined by $^1$H-NMR and IR spectroscopy. Elemental analysis gave the following values:
C: calculated: 77.3% by weight; found: 77.1% by weight
H: calculated: 7.2% by weight; found: 7.3% by weight
N: calculated: 4.7% by weight; found: 5.1% by weight

Example 3

The procedure was similar to that of Example 1, but the amine used was 198 g (0.85 mol) of 4-tert-butyl-2,6-diisopropylaniline.

222 g of a pale-brown crude product having an NCO content of 16.1% by weight (calculated 16.2% by weight), a purity, determined by gas chromatography, of 97.8% by weight, a content of hydrolyzable chlorine of 127 ppm and a viscosity, measured at 25° C. by the Ubbelohde method, of 40 mPas, were obtained.

The resultant crude product was purified by distillation under reduced pressure, giving 4-tert-butyl-2,6-diisopropylphenyl isocyanate as a clear, colorless liquid which boils at 86° C./0.5 mbar, in a yield of 98.2% of theory.

The structure was determined by $^1$H-NMR and IR spectroscopy. Elemental analysis gave the following values:
C: calculated: 78.7% by weight; found: 78.4% by weight
H: calculated: 9.7% by weight; found: 9.7% by weight
N: calculated: 5.4% by weight; found: 5.7% by weight Preparation of 4,4'-disubstituted (2,6-diisopropylphenyl carbodiimides

Example 4

100 parts by weight of 4-(1-methyl-1-phenyl-ethyl)-2,6-diisopropylphenyl isocyanate prepared in accordance with Example 1 were heated to from 160° to 170° C. in the presence of 0.1 part by weight of 1-methyl-2-phospholene 1-oxide and in the absence of a solvent, and the mixture was condensed in this temperature range with vigorous evolution of carbon dioxide. When an NCO content in the reaction mixture of less than 1% by weight had been reached, for which a reaction time of approximately 14-hours was necessary, the added catalyst and residues of unreacted 4-(1-methyl-1-phenylethyl)-2,6-diisopropylphenyl isocyanate were removed by distillation at 180° C./0.1 mbar, giving 92.1 parts by weight of bis(4-(1-methyl-1-phenylethyl)-2,6-diisopropylphenyl)carbodiimide having an NCO content of less than 0.4% by weight, a content of -N═C═N groups of 65 mg/g and a melting point of 59° C. This corresponds to a yield of 98.9% of theory.

Its structure was determined by $^1$H-NMR and IR spectra.
Elemental analysis gave the following values:
C: calculated: 86.2% by weight; found: 85.9% by weight
H: calculated: 9.1% by weight; found: 8.9% by weight
N: calculated: 4.7% by weight; found: 4.9% by weight

Example 5

The procedure was similar to that for Example 4, but the isocyanate used was 100 parts by weight of 4-phenoxy-2,6-diisopropylphenyl isocyanate prepared in accordance with Example 2.

The distillation residue obtained comprised 90.7 parts by weight of bis(4-phenoxy-2,6-diisopropylphenyl)-carbodiimide having an NCO content of less than 0.4% by weight, a content of -N═C═N groups of 71 mg/g and a melting point of 70° C. This corresponds to a yield of 98.1% of theory.

Its structure was determined by $^1$H-NMR and IR spectra.
Elemental analysis gave the following values:
C: calculated: 81.3% by weight; found: 81.0% by weight
H: calculated: 7.7% by weight; found: 7.5% by weight
N: calculated: 5.1% by weight; found: 5.4% by weight

Example 6

The procedure was similar to that for Example 4, but the isocyanate used was 100 parts by weight of 4-tert-butyl-2,6-diisopropylphenyl isocyanate prepared in accordance with Example 3.

The distillation residue obtained comprised 90.1 parts by weight of bis(4-tert-butyl-2,6-diisopropylphenyl)carbodiimide having an NCO content of less than 0.4% by weight, a content of -N═C═N groups of 81 mg/g and a melting point of 80° C. This corresponds to a yield of 98.5% of theory.

Its structure was determined by $^1$H-NMR and IR spectra.
Elemental analysis gave the following values:
C: calculated: 83.5% by weight; found: 83.2% by weight
B: calculated: 10.6% by weight; found: 10.4% by weight
N: calculated: 5.9% by weight; found: 6.1% by weight Preparation of carbodiimide-stabilized thermoplastic polyurethanes (TPUs)

Examples 7 to 13 and Comparative Examples I to III

A mixture of 1000 parts by weight (0.5 mol) of a 1,4-butanediol 1,6-hexanediol polyadipate having a hydroxyl number of 56 and n% by weight of one of the carbodiimides mentioned below was dried for one hour at 110° C./2 mbar.

113 parts by weight (1.26 mol) of 1,4-butanediol were added to the mixture, which was then warmed to 70° C., and 440 parts by weight of a melt, heated to 65° C., of 4,4'-diphenylmethane diisocyanate were added with vigorous stirring.

When a reaction temperature of 120° C. had been reached, the homogeneous reaction mixture was poured onto a metal plate held at 125° C. After approximately 2 minutes, the hot crude product was removed from the metal plate, coarsely comminuted and then conditioned at 100° C. for 15 hours. The resultant TPU, which had a Shore hardness of 85 A, was cooled, granulated and then injection-molded to give test specimens.

In order to carry out a standardized hydrolysis test, the test specimens were stored in demineralized water at 80° C., and the tensile strength and elongation at break were re-measured in accordance with DIN 53 504 after 42 days.

The 4-substituted bis(2,6-diisopropylphenyl)carbodiimides used and the carbodiimides employed as comparative products, their amounts in % by weight, and the tensile strength and elongation measured on the test specimens are shown in the table below.

TABLE

| | Carbodiimide | | Tensile strength after days | | Elongation at break after days | |
|---|---|---|---|---|---|---|
| | Type | Amount [% by wt.] based on TPU | 0 [MPa] | 42 [MPa] | 0 [%] | 42 [%] |
| Example | | | | | | |
| 7 | bis(4-(1-methyl-1-phenyl-ethyl)-2,6-diisopropyl-phenyl)carbodiimide | 0.65 | 53 | 40 | 610 | 680 |
| 8 | bis(4-(1-methyl-1-phenyl-ethyl)-2,6-diisopropyl-phenyl)carbodiimide | 1.0 | 44 | 36 | 540 | 600 |
| 9 | bis(4-(1-methyl-1-phenyl-ethyl)-2,6-diisopropyl-phenyl)carbodiimide | 1.3 | 44 | 37 | 570 | 670 |
| 10 | bis(4-phenoxy-2,6-diiso-propylphenyl)carbodiimide | 0.65 | 48 | 33 | 550 | 760 |
| 11 | bis(4-phenoxy-2,6-diiso-propylphenyl)carbodiimide | 1.0 | 47 | 31 | 540 | 790 |
| 12 | bis(4-tert-butyl-2,6-diisopropylphenyl)-carbodiimide | 0.65 | 49 | 41 | 530 | 770 |
| 13 | bis(4-tert-butyl-2,6-diisopropylphenyl)-carbodiimide | 1.0 | 42 | 42 | 510 | 850 |
| Comparative Example | | | | | | |
| I | di(2,6-diisopropyl-phenyl)carbodiimide | 0.65 | 51 | 33 | 490 | 710 |
| II | polycarbodiimide, prepared from 1,3-diisocyanato-2,4,6-triisopropylbenzene | 0.65 | 54 | 7 | 610 | 420 |
| III | unstabilized TPU | — | 51 | destroyed | 590 | destroyed |

We claim:

1. A 4-substituted 2,6-diisopropylphenyl isocyanate of the formula (II)

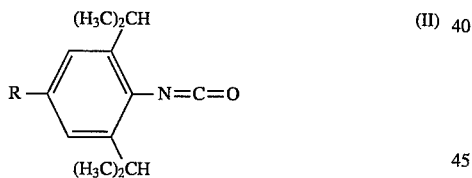

where R is phenyl.

* * * * *

UNITED STATES PATENT AND TRADEMARK OFFICE
CERTIFICATE OF CORRECTION

PATENT NO.   : 5,621,138
DATED        : April 15, 1997
INVENTOR(S)  : Friedhelm Lehrich et al It is certified that error appears in the above-indentified patent and that said Letters Patent is hereby corrected as shown below:

In claim 1, last line, replace "phenyl" with --phenoxy--.

Signed and Sealed this

Second Day of September, 1997

Attest:

BRUCE LEHMAN

Attesting Officer

Commissioner of Patents and Trademarks